(12) United States Patent
Terzis et al.

(10) Patent No.: US 11,879,227 B2
(45) Date of Patent: Jan. 23, 2024

(54) SYSTEM AND METHOD FOR GROUND CONSOLIDATION

(71) Applicant: ECOLE POLYTECHNIQUE FEDERALE DE LAUSANNE (EPFL), Lausanne (CH)

(72) Inventors: Dimitrios Terzis, Nyon (CH); Lyesse Laloui, Ecublens (CH); Patrick Hicher, Préverenges (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 178 days.

(21) Appl. No.: 17/615,532

(22) PCT Filed: May 31, 2019

(86) PCT No.: PCT/IB2019/054532
§ 371 (c)(1),
(2) Date: Nov. 30, 2021

(87) PCT Pub. No.: WO2020/240263
PCT Pub. Date: Dec. 3, 2020

(65) Prior Publication Data
US 2022/0228340 A1 Jul. 21, 2022

(51) Int. Cl.
*E02D 3/11* (2006.01)
*E02D 3/12* (2006.01)
(Continued)

(52) U.S. Cl.
CPC ................ *E02D 3/11* (2013.01); *C09K 17/42* (2013.01); *C12N 1/20* (2013.01); *C12N 9/80* (2013.01); *C12N 13/00* (2013.01); *C12P 3/00* (2013.01); *C12Y 305/01005* (2013.01); *E02D 3/12* (2013.01)

(58) Field of Classification Search
CPC .. E02D 3/11; E02D 3/12; C09K 17/42; C12N 1/20; C12N 9/80; C12N 13/00; C12Y 305/01005
See application file for complete search history.

(56) References Cited

U.S. PATENT DOCUMENTS

| 4,162,707 A | 7/1979 | Yan |
| 5,616,235 A | 4/1997 | Acar |

(Continued)

FOREIGN PATENT DOCUMENTS

| CN | 103276719 B | 9/2013 |
| CN | 105220681 | 1/2016 |

(Continued)

OTHER PUBLICATIONS

DeJong JT, Soga K, Kavazanjian E, Burns S, Van Paassen LA, Al Qabany A, Aydilek A, Bang SS, Burbank M, Caslake LF, Chen CY, Biogeochemical processes and geotechnical applications: progress, opportunities and challenges, Geotechnique, Mar. 1, 2013;63(4):287.

(Continued)

*Primary Examiner* — Janine M Kreck
(74) *Attorney, Agent, or Firm* — Maschoff Brennan

(57) ABSTRACT

The present invention relates to a method for inducing ground consolidation. The method comprises providing a first chamber in a first hole in the ground, and a second chamber in a second hole in the ground, the first and second chambers being liquid-impermeable and electrically conductive; providing a first electrolytic fluid in the first chamber and a second electrolytic fluid in the second chamber; placing at least a first electrode in the first chamber, and at least a second electrode in the second chamber, the first and second electrodes being operatively connected to a power supply; feeding consolidation fluids into the ground for feeding reactants of a consolidation process, and catalysers for the reactants into the ground; and applying to the first and (Continued)

second electrodes an electric current. The current causes the first electrode to operate as an anode and the second electrode to operate as a cathode thereby inducing electric polarization in the ground to cause the reactants and catalysers to cross paths to thereby cause consolidation of the ground.

20 Claims, 4 Drawing Sheets

(51) Int. Cl.
*C12P 3/00* (2006.01)
*C09K 17/42* (2006.01)
*C12N 1/20* (2006.01)
*C12N 13/00* (2006.01)
*C12N 9/80* (2006.01)

(56) References Cited

U.S. PATENT DOCUMENTS 9,328,473 B2 * 5/2016 Esnault .................. C09K 17/42
2014/0377014 A1 12/2014 Esnault

FOREIGN PATENT DOCUMENTS

| | | |
|---|---|---|
| CN | 104631430 B | 6/2016 |
| CN | 105970913 B | 9/2016 |
| CN | 106368207 | 2/2017 |
| CN | 104790378 B | 3/2017 |
| DE | 602005000788 | 1/2008 |
| JP | H10-110426 A | 4/1998 |
| JP | 2006346549 | 12/2006 |
| WO | 00/70152 A1 | 11/2000 |
| WO | 2006066326 A1 | 6/2006 |
| WO | 2008120979 | 10/2008 |

OTHER PUBLICATIONS

Hausinger RP (2013) Biochemistry of Nickel, Springer Science & Business Media, USA (Full Book).
Mitchell, J. K., & Santamarina, J. C. (2005), Biological considerations in geotechnical engineering, Journal of geotechnical and geoenvironmental engineering, 131(10), 1222-1233.
Ground Improvement Case Histories, Chemical, Electrokinetic, Thermal and Bioengineering, ISBN 978-0-08-100191-2, 2014, Chapter 14 (Amnart Rittirong, Julie Shang) (Full Book).

* cited by examiner

SYSTEM AND METHOD FOR GROUND CONSOLIDATION

TECHNICAL FIELD

The present invention belongs to the fields of construction technology and geotechnical engineering. More precisely, the present invention relates to a method and system for ground stabilization by using a system of electrodes in the ground.

BACKGROUND ART

Ground stabilization is a major branch of geotechnical engineering, which deals with the improvement of the mechanical properties of soils. Such works are necessary in the majority of construction applications and they have become all the more relevant given increasing scarcity of suitable land for development. In addition, extreme weather phenomena of increasing intensity often trigger infrastructure failures by causing soil erosion or landslides, for example. Ground stabilization is therefore necessary during implementation of construction works to mitigate stability risks or it can be also implemented during service life of infrastructure for repair purposes.

Various techniques are currently available for implementing ground stabilization. These techniques typically use at their core either cement or chemical fluids. These species are introduced into the ground by pressurized mixing with soil or by infiltration of the ground at various speeds. However, flushing soils with reactive solutes under low pressure is possible for geo-materials which have a hydraulic conductivity in the range of around $10^{-1}$ to $10^{-5}$ cm/sec. For finer soils, such as geo-materials which are rich in silt or clay, the hydraulic conductivity values remain below $10^{-6}$ cm/sec. This hinders infiltration of the subsurface and requires high pressure to be applied, which reach up to 40 MPa (400 bars). Generating such a high pressure results in high on-site energy demands and therefore in increased overall cost of application. To facilitate the distribution of solutes through fine soils, electrodes may be used to apply an electric field of fixed or alternating polarization. In other words, a direct current is applied in the soil volume for the purpose of removing pollutants from the soil volume.

More recently, biology has been mobilized to improve ground properties and to increase ground resistance. More precisely, bacteria can be introduced into the ground to stimulate for instance chemical reactions such as the hydrolysis of urea, which results in the production of carbonate anions able to react with calcium cations to form calcium carbonate ($CaCO_3$). This process may occur in many natural environments where microorganisms are present. The technique has gained momentum during the past decade in scientific literature and industrial practice.

The above processes may be used for providing consolidation solutions for soils, for stabilizing earth slopes prone to landslide movements, for restoring weak and collapsible soils and for mitigating liquefaction risks.

Electro-kinetics has been used for inducing cementation in porous media or for removing pollutants from soils. These approaches, however, ignore the beneficial presence of biological species as described above which hold a catalyzing role in reactive and transport phenomena, and can possibly accelerate significantly the involved processes to render these reactions applicable within typical timeframes, confronted in construction practice.

The combined use of biological and nutrient species with electric currents to alter soil structures is also known. However, these solutions do not account for a method and system to bypass the detrimental effect of direct currents on the pH of the flushed liquid solutions and on the desired soil calcification. If the desired result of the soil treatment is its cementation, calcification or stabilization by producing solid minerals, such as calcium carbonate particles, in the soil, then acidic conditions caused by application of direct currents in the soil and in the groundwater need to be avoided. More precisely, direct current results in electrolysis of water. This means that $H_2O$ is decomposed into oxygen gas, which is produced at the anode (the chemical balance equation of water oxidation at the anode is $2H_2O \rightarrow O2(g)+4H^++4e^-$ that shows the generation of the acidic front), and into hydrogen gas, which is produced at the cathode. Therefore, acidic conditions are generated at the anode. This means that carbonic species, including cementitious elements and calcium carbonate, are dissolved and any bacterial and enzymatic activity ceases.

SUMMARY OF INVENTION

It is an object of the present invention to overcome at least some of the problems identified above related to ground consolidation solutions.

In order to address and overcome at least some of the above drawbacks of the prior art solutions, the present invention proposes a new method and system for inducing consolidation, e.g. by calcification, of a ground volume having improved features and capabilities.

According to a first aspect of the invention, there is provided a ground consolidation method as recited in the claims.

According to a second aspect of the invention, there is provided a ground consolidation system as recited in the claims.

Thus, the present invention describes a chamber-based solution, where the chambers accommodate electrodes but prohibit fluid exchanges between electrolysed liquids and the ground which is targeted for the treatment. A respective chamber comprising at least one electrode retains electrolysis within its body and prohibits acidification and gas generation in the ground volume while inducing electric polarization in its vicinity. The proposed solution, which electrically polarizes the ground volume, and which does not create any direct currents (or slowly alternating currents) or Faradaic currents (electron transfer by means of electrochemical reaction)) in or through the ground, allows stimulating the distribution and attachment of biological species (acting as catalysers) prior to inducing flow trajectories for chemical species (acting as reactants). In this manner, the ground can be efficiently solidified by producing consolidated geo-materials. Thus, the proposed geotechnical engineering solution efficiently uses catalysers, such as enzymes, to achieve a fast and homogenous consolidation of the ground with low permeability.

Additionally, the present invention may also be used to provide a method which combines preparation, application, monitoring and subsequent quality control of the treated ground volume in a single setup. For instance, boreholes for the chambers are drilled vertically or in inclined setups (in slopes for example) for installation of electrodes into the ground such that some of the electrodes act as anodes while the other electrodes act as cathodes. According to the present invention, the system of electrodes can be used as a means of flushing efficiently the surrounding ground volume with enzymes and reactive solutes. Furthermore, the same system can serve as a means of attracting byproducts to the anode or cathode end for their efficient extraction (by suction for instance) and for their subsequent recycling. Additionally, once consolidation of the ground is achieved, the employed electrodes may be removed from the ground and in their place monitoring devices or additional ground stabilization elements, such as soil nails and drainage systems, may be installed.

By flushing, for example, enzymes or microorganisms, such as urease-bearing germs, through the ground, a bio-geological system can be created to firstly induce, and subsequently control, the spatial distribution of solidified minerals resulting from the distribution of solutes in the ground. Microorganisms are characterized by their negatively charged cell walls and, under the right conditions, they can attach efficiently to soil particles and grow communities or biofilms, which act as nucleation sites for the subsequent precipitation of minerals, such as solid calcium carbonate. Therefore, the present invention advantageously may use biological catalysers which can greatly enhance the evolution and efficiency of electro-kinetic stabilization of soils. In one example, the soil is flushed with urease enzyme acting as a catalyser, which is produced in-vivo or in-vitro by several microorganisms or algae or can be released by degraded bacteria cells, following their cell wall breakdown. Microbiologically induced calcium carbonate precipitation (MICP) is a natural process and is based on microbial-induced urea hydrolysis (Equation 1). This natural reaction mechanism is catalyzed e.g. by the enzyme urease found in several bacterial strains. In other words, bacteria are used as a catalyser in the reaction. A catalyzed urea hydrolysis completes $10^{14}$ times faster compared to a non-catalyzed reaction. This renders the reaction feasible within typical timeframes of construction projects. The available bicarbonate ($CO_3^{2-}$) produced by the urea hydrolysis precipitates into solid calcium carbonate crystals (Equation 2) under the presence of a calcium source, such as calcium chloride.

$$CH_4N_2O + 2H_2O \rightarrow 2NH_4^+ + CO_3^{2-} \quad (1)$$

$$Ca^{2+} + CO_3^{2-} \rightarrow CaCO_3\downarrow \quad (2)$$

Externally imposed flows of reactive fluids are applied to soils to improve their properties. Suitable pore fluid chemistry can be coupled with biology leading to fast consolidation of the porous media resulting in increased overall mechanical resistance. However, fine soils, such as clays with strong electrochemical interactions among their particles, hinder hydraulic transport of solutes. By mobilizing a system of electrodes to generate electric polarization of the ground volume, the penetration and propagation of these solutes or reactants can be greatly assisted through a controlled flow trajectory by avoiding direct electric currents through the ground, which would have detrimental effects on the desired calcification or consolidation more broadly. Bacterial and/or ionic species acting as catalysers can be flushed through the ground at various speeds when electrodes are placed at various distances within specific chambers. The cations and anions (i.e. the solutes) are ideally injected respectively in the vicinity of the anode and cathode of the generated electric polar system and flow through the ground. Within the anode, electrolysis occurs and the anode together with its chamber and electrolytic fluid acts as a positive pole to attract anions and repel cations. In other words, cations (with a net positive charge) are attracted towards the negative electric pole or terminal (cathode) while anions (with a net negative charge, which is opposite to the charge of a cation) flow towards the positive electric pole or terminal (anode). It is to be noted that the anode and cathode may be defined as for example given in the book "Ground Improvement Case Histories", Chemical, Electro-kinetic, Thermal and Bioengineering, ISBN 978-0-08-100191-2, 2014, Chapter 14 (Amnart Rittirong, Julie Shang). When these species flush across the target medium and cross paths under the presence of catalysers, such as certain enzymes or microbial species, a solidified structure is homogenously formed in the ground. Moreover, the installation and use of electrodes can provide additional means of long-term ground stabilization and monitoring since drilled boreholes can be alternatively used as drainage systems or soil anchors.

Other aspects of the invention are recited in the dependent claims attached hereto.

BRIEF DESCRIPTION OF DRAWINGS

Other features and advantages of the invention will become apparent from the following description of a non-limiting example embodiment, with reference to the appended drawings, in which.

DETAILED DESCRIPTION OF AN EMBODIMENT OF THE INVENTION

Figure 1:
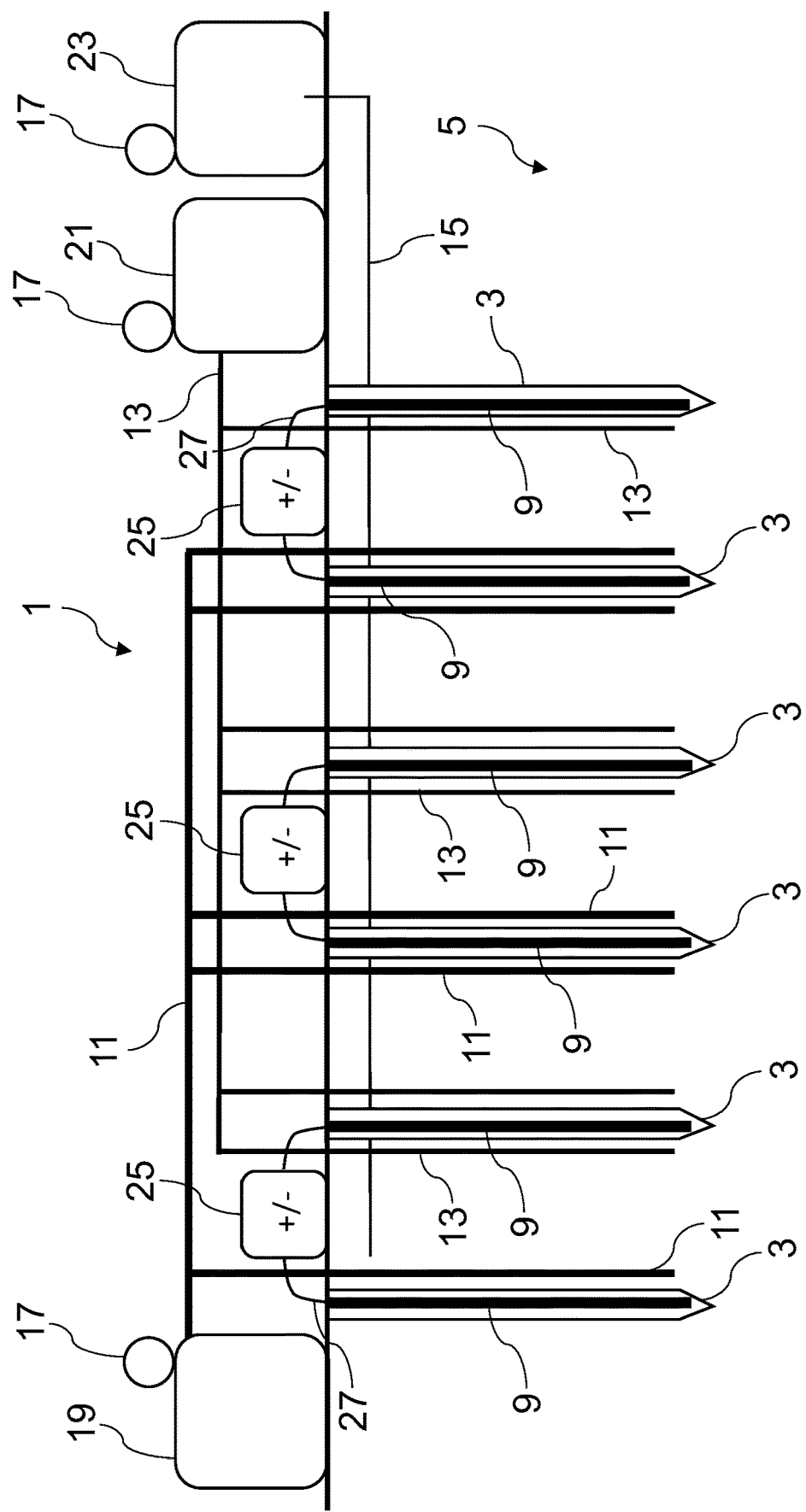
FIG. 1 schematically illustrates in a side view a ground consolidation system according to an example of the present invention.

An embodiment of the present invention will now be described in detail with reference to the attached figures. This embodiment is described in the context of solidifying ground through generation of calcium carbonate, but the teachings of the invention are not limited to this environment. Identical or corresponding functional and structural elements which appear in the different drawings are assigned the same reference numerals.

The present invention in the following example embodiment describes an application method according to which a system of electrodes is used for improving the stability and/or mechanical properties of geomaterials, such as various types of soil, sand, gravel, silts, clays, through hydraulic and electro-migration of bio-chemical reactive flows. Thus, the proposed system may be considered as a system of electrodes for bio-chemo-geological use.

Figure 4:
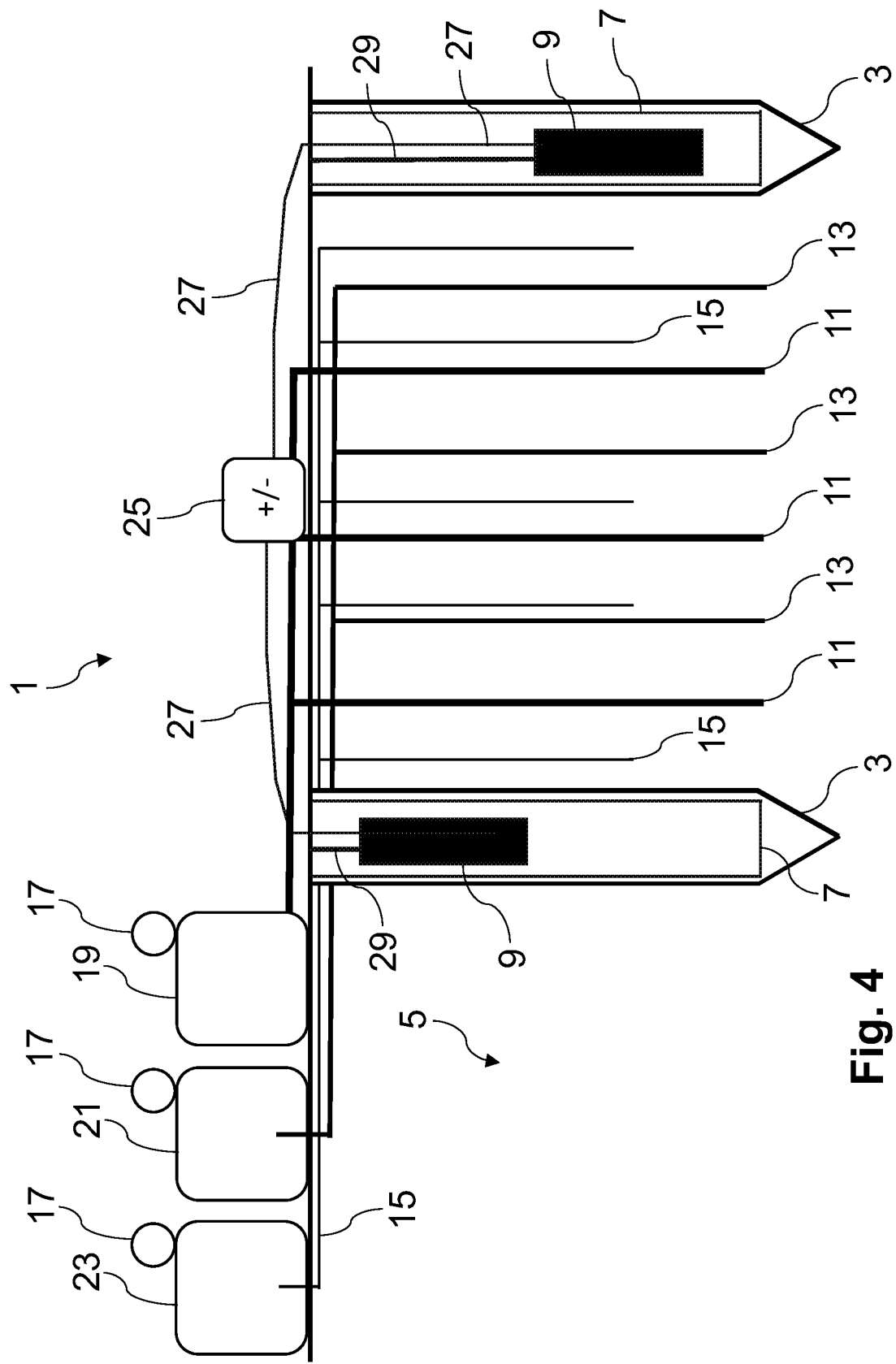
FIG. 4 schematically illustrates in a side view yet another configuration of the ground consolidation system when applied in a substantially even and horizontal environment.

FIG. 1 schematically illustrates a geomaterial consolidation system 1 comprising a set of holes 3, such as boreholes, in the ground 5, each borehole being configured to at least partially receive a case or chamber 7 (shown in FIG. 4). The boreholes may be created by drilling longitudinal blind holes in the ground. The chambers may be shaped and sized to substantially match the shape and size of the boreholes. Thus, a respective chamber may occupy substantially the entire volume of a respective borehole as seen in FIG. 1. Alternatively, a respective chamber can occupy a part of a respective borehole volume at a fixed or varying position along a longitudinal axis of the respective borehole. An array or a set of electrodes 9 is placed into each chamber. In this example, one chamber includes one electrode. A respective chamber 7 also comprises an electrolysable or electrolytic fluid. In this example, the chambers are filled with these fluids.

The consolidation system 1 also comprises a flow or pipe network or system for circulating fluids or liquids and more specifically for feeding solutes (also referred to as reactants) and catalysers or catalysts into the ground. In the present description, by a consolidation fluid is understood any one of the fluids used in the proposed process. The fluids, which may be water-based or aqueous fluids or more specifically liquids, collectively or together comprise the solutes and the catalysers. More specifically, the consolidation fluids may individually or collectively comprise any combination of the following species: biological, nutrient and chemical species. A first flow or pipe system 11 comprising first pipes is used for feeding a first solute fluid (comprising a first type of reactants) into the ground 5, while a second flow or pipe system 13 comprising second pipes is used for feeding a second, different solute fluid (comprising a second type of reactants) into the ground 5. The first and second flow systems may be also used for feeding a catalyser fluid into the soil. Alternatively, a third flow or pipe system 15 comprising third pipes may be provided for feeding a catalyser fluid in this example comprising enzymatic catalysers into the ground as shown in the figures. In the configuration of FIG. 1, a portion of the first pipes and a portion of the second pipes are arranged substantially parallel to the chambers and thus they extend into the ground from the surface, optionally substantially orthogonal to the ground surface. Furthermore, the pipes supplying a calcium-based solute (i.e. cations) are arranged in close proximity to the anodes acting as the positive poles possibly together with the electrode chamber and its electrolytic fluid to be able to inject cations close to the positive poles, while the pipes supplying a carbon-based solute (i.e. anions) are arranged in close proximity to the cathodes acting as the negative poles possibly together with the electrode chamber and its electrolytic fluid to be able to inject the anions close to the negative poles. In this example, a portion of the third pipes are arranged substantially parallel to the soil surface. However, instead, they could also extend into the ground, optionally substantially orthogonal to the ground surface.

The pipes 11, 13, 15 comprise a set of openings, orifices or through holes on their periphery longitudinally along the portion of the pipes that are in the ground to allow the solutes and/or catalysers to escape the pipes so that they can be fed into the soil by gravity and/or by using pumps 17, which in this example are peristaltic pumps. The set of openings thus comprises only one opening or multiple openings. The largest cross-sectional dimension (e.g. a diameter) of a respective opening may be between 0.5 mm to 10 cm or more specifically between 1 mm and 10 mm or between 1 mm and 5 mm. Alternatively or in addition, the pipes may have an outlet, optionally at the end of the pipes which is located in the ground during the use of the system 1. The pumps 17 may operate as injection or collection (extraction) pumps as explained later in more detail. Thus, the supply of water, which in this example is rich in enzymatic calcification catalysers and chemical solutes is carried out by the pumps 17, which are connected to supply tanks. The pressure applied by the pumps may vary between zero (i.e. gravity flow conditions) to hundreds of bars or tens of MPa. In this example, the first solute fluid is stored in a first reservoir 19, supply system or tank, the second solute fluid is stored in a second reservoir 21, supply system or tank and the catalyser fluid is stored in a third reservoir 23, supply system or tank. However, it would also be possible to have only two tanks instead of three tanks. In this case, the catalyser fluid could be stored together with either the first solute fluid or together with the second solute fluid or with both the first and second solute fluids. The first flow system 11 is thus connected to the first tank 19, the second flow system 13 is connected to the second tank 21, while the third flow system 15 is connected to the third tank 23. More specifically, an inlet of a respective flow system is connected to a respective tank. The chambers are equipped with a membrane or another surface or element which is sufficiently electrically conductive to transfer electric charge and which is impermeable in order to prohibit fluid exchanges between electrolysed fluids present in the chambers 7 and the consolidation fluids which are injected to the ground 5 through the flow network, which is connected to the external supply systems.

The consolidation system 1 also comprises one or more electric power sources 25 or generators, such as current sources, for electrically supplying the electrodes 9 in the chambers 7. The power sources are connected to the electrodes through wires 27. In this example, each electrode set pair is supplied by its dedicated power source. In this example, the power sources operate as direct current power generators, but they could produce a slowly alternating current instead. During operation of the system, the electrode sets are supplied so that they form anode-cathode pairs. More specifically, referring to FIG. 1, one of the electrode sets of a pair operates as an anode, while the other electrode set operates as a cathode. In this example, the electrodes are configured to be movable, i.e. they can be removed from the chambers. In the example shown in FIG. 1, the length of the electrodes substantially equals the length of the boreholes. However, this does not have to be the case. More specifically, the electrodes may be arranged to move along the longitudinal axis of the borehole, i.e. in the configuration of FIG. 1 they could move up and/or down. For this purpose, a respective electrode or electrode set can be connected to a cable 29 (as shown in FIG. 4) or support means or member to position the electrode or electrode set in a desired position in the borehole 3.

Figure 2:
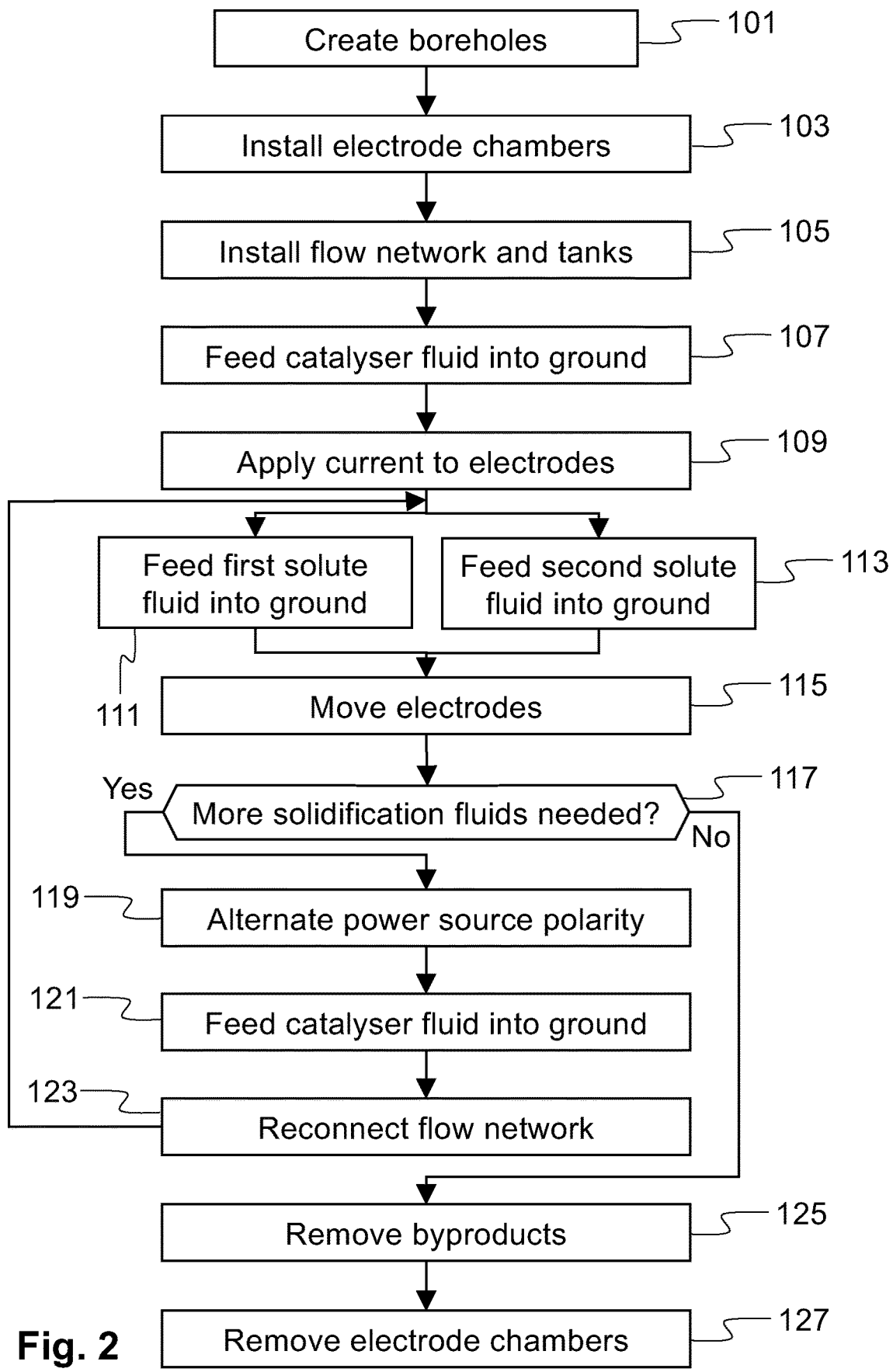
FIG. 2 is a flow chart summarizing a ground consolidation method according to an example of the present invention.

The operation of the system 1 according to one example is next explained in more detail with reference to the flow chart of FIG. 2. In step 101, the holes are created in the ground by e.g. drilling and/or digging. In step 103, the chambers are placed in the ground holes and then subsequently the electrodes 9 and the electrolytic fluids are placed in the chambers. Different chambers may accommodate the same electrolytic fluid or these fluids may be different. Additionally, buffer solutions can be mixed in the chambers to adjust the pH of the respective fluid and to prevent corrosion of the external metallic wall or that of the membrane. In step 105, the flow network and the tanks are installed and the tanks are filled or partially filled with a fluid they are designed to hold. The pipes 11, 13, 15 of the flow network may be directly pushed into the ground or channels may be made for them in the ground to facilitate their insertion into the ground by placing the pipes at least partially into the created channels. In step 107, the catalyser fluid is fed or supplied into the ground, in this example through the third flow system 15.

In step 109, direct current is applied to the electrodes in the chambers. Consequently, anode-cathode electrode pairs are formed and the electrolytic fluids become electrolysed. Various power sources can work simultaneously or individually by supplying electric current to the electrodes through fixed or varying current intensity and/or fixed or alternating polarity. The application of the current also causes electric polarization of the ground between the electrodes and in their vicinity. By electric polarization is understood a slight relative shift of positive and negative electric charge in opposite directions within an insulator, or dielectric (or in another substance), induced by an external electric field. Polarization typically occurs when an electric field distorts the negative cloud of electrons around positive atomic nuclei in a direction opposite the field. Polarization P in its quantitative meaning is the amount of dipole moment p per unit volume V of a polarized material, i.e. P=p/V. An insulator or a dielectric, such as soil, is understood to be insulating material or a very poor conductor of electric current. When dielectrics are placed in an electric field, practically no current flows in them because, unlike metals, they have no loosely bound, or free, electrons which may drift through the material. Electric polarization occurs instead. The positive charges within the dielectric are displaced in the direction of the electric field, and the negative charges are displaced in the direction opposite to the electric field. This slight separation of charge, or polarization, reduces the electric field within the dielectric and enhances the surface charge density, thus favouring electrostatic interaction at the solid particles-solute interface (attachment of microorganisms and calcium attraction). The application of the direct current also causes the catalysers of the catalyser fluid to diffuse in the ground and attach onto ground particles. In other words, the electric field across the ground volume stimulates the diffusion and attachment of the catalysers, such as enzymes, onto ground particles.

In step 111, the first solute fluid is fed into the ground through the first flow system 11, and optionally at the same time, in step 113, the second solute fluid is fed into the soil through the second flow system 13. In this example, the first solute fluid is the source of cations while the second solute fluid is the source of anions. More specifically, the first solute fluid may comprise calcium compound particles, such as calcium chloride, calcium acetate, calcium lactate, calcium hydroxide or calcium nitrate or any combination thereof. The first solute fluid is thus a calcium source. The second solute may comprise urea and is thus a carbon source. In the example of FIG. 1, the first and second flow systems are arranged such that the first flow system supplies cations to the vicinity of the positive poles, while the second flow system supplies anions to the vicinity of the negative poles. In the configuration of FIG. 1, the electrode on the left (together with its chamber and electrolytic fluid) of a given electrode pair operates as a positive pole, while the electrode on the right (together with its chamber and electrolytic fluid) of a given electrode pair operates as a negative pole. In the ground, the cations and anions are driven respectively towards the negative poles and positive poles under the influence of the electric field in the soil. More specifically, the positive poles attract the anions but repel the cations while the negative poles attract the cations but repel the anions. When the paths of the solutes and catalysers cross, precipitation of cementitious-like minerals occurs, such as solid calcium carbonate, causing the ground to solidify. By adjusting the salinity and nutrient composition of the solute(s), attachment and growth of biological species can be enhanced. In other words, the chemical concentrations of the fluids can be adjusted or varied based on the target substance to be solidified and/or the desired application (i.e. the consolidation target). This is for example achieved by adding calcium lactate, peptone and/or calcium acetate.

In operation of the system 1, the electrodes 9 induce electric polarization of the ground volume and thus also an electromagnetic field in the ground volume, without however generating direct current or slowly alternating current through the ground volume. The field can thus be used for successfully seeding bacteria in the ground in predetermined locations and for enhancing their attachment to the medium's particles. The presence of catalytic bacteria or their products, such as enzymes, can be beneficial for accelerating reactions which results in the production of mineral species, such as calcite. This results in hardening of the ground and overall improved resistance. However, if the consolidation is not homogenous, a part of the treated ground remains weak and thus cannot sustain loads imposed by structures or other environmental threats. Therefore, the proposed system of electrodes is particularly beneficial since it enables propagating biological catalysers which offer fast and homogenous production of cementitious-like minerals and ensures the durability of these minerals by avoiding water electrolysis caused by direct currents.

In step 115, the electrodes are displaced or moved to improve even distribution of the catalysers and/or solutes in the ground. However, if the electrodes are long enough to occupy longitudinally substantially the entire length of the chamber as in the configuration of FIG. 1, then there is no need to move them. More specifically, if the electrodes are shorter than the length of the chambers, then the electrodes can be moved along the longitudinal axis of the chambers, i.e. in the configuration of FIG. 1 they would be moved up and/or down. The electrodes may be first moved in a first direction and then stopped for a first time duration. After this, they may be moved again in the first direction or in a second direction, which is substantially opposite to the first direction, and then stopped again for a second time duration, which may or may not equal the first time duration, before they may be moved again. The exact movement pattern may depend on the target substance and/or the desired application. It is to be noted that it would also be possible to move the electrodes in a direction which is substantially orthogonal to the longitudinal axis of the chambers if there is sufficiently place in the chambers. However, this direction of movement would typically have less impact on the even distribution of the solutes and/or catalysers.

In step 117, it is determined whether or not more consolidation fluid(s) is/are needed. In other words, in this step, it is determined whether or not more ground consolidation is needed. If more fluids are needed, then in step 119, the polarity of at least one of the power sources 25 is reversed. In this example, the polarity of all the power sources in the system is reversed. More specifically, the system of electrodes is supplied electric current by the power sources 25, which can alternate the functional role of individual electrode probes between negative and positive poles. The DC current alternation further enhances even distribution of the consolidation fluid in the ground and thus even distribution of the solutes and catalysers. In this manner, substantially even consolidation of the soil can be achieved. In step 121, more catalyser fluid is introduced into the ground. In step 123, the flow network is reconnected so that the first flow system 11 is connected to the second tank 21 while the second flow system 13 is connected to the first tank 19. In this manner it can be ensured that during subsequent solute feeding steps, the solutes are fed to optimal locations in the ground. The process then continues in steps 111 and 113 where more solute fluids are introduced into the ground.

If in step 117 it was determined that no more fluids are needed, then in step 125, byproducts or secondary products of the ground consolidation are removed. More specifically, an alternative functional role of the system 1 illustrated in FIG. 1 can follow its initial use as a bio-chemical consolidation mechanism. Once bio-chemical consolidation is achieved as a result of carrying out steps 101 to 123, the electrodes 9 can remain in the ground and keep generating the electric polarization in the ground in order to treat byproducts. For example, a third solute fluid comprising base cations may be fed into the ground, optionally in the vicinity of the cathodes. The base cations are thus allowed to be diffused towards the anodes to assist the removal of the byproducts through ammonium oxidation or gas generation, for example. The third solute may thus comprise a pH buffer configured to neutralize ammonia. Alternatively or in addition, biological species can be introduced into the ground to catalyze ammonium oxidation in the ground, which is electrically polarized by the system of electrodes. The generated gases escape the ground without any further action being taken, while the other generated byproducts may be sucked way from the ground by using one or more of the flow systems. In the case of water or other liquid extraction by using the flow network and the pumps, the tube endings in the ground or the pipe openings may act as inlets which collect the water and supply it to a respective tank through an outlet connected to the respective tank. A fourth reservoir, supply system or tank may be provided for holding the third solute fluid such that one or more of the flow systems may be connected to the fourth tank for carrying out step 125. Alternatively, a dedicated flow system (a fourth flow system) may be provided for introducing the third solute fluid into the ground.

In step 127, the electrodes 9 are removed from the ground. More specifically, upon completion of the desired consolidation of the ground volume, the electrodes 9, optionally together with the electrolysed fluids and/or chambers 7, are removed from the ground and the boreholes 3 can be re-filled with soil or accommodate drains, nails, cement or other filling material. The electrodes can thus be removed from the system and be reused in future applications. The boreholes may also be filled with elements which add additional stability to the ground, such as resins or metallic reinforcements. Another use of these boreholes is to host monitoring devices for quality control and long-term assessment of stability risks.

It is to be noted that in the method described above, some steps, such as steps 117 to 127, are optional. Furthermore, the order of at least some of the steps may be changed. For instance, the current may be applied to the electrodes only once the first, and second solute fluids and the catalyser fluid are fed into the ground. Furthermore, it is possible to supply the catalyser fluid into the ground only after the first and second solute fluids are injected into the ground. The method may also comprise additional steps. For instance, it is possible to feed a stimulation fluid into the ground for stimulating the activity of the catalysers. The simulation fluid may comprise e.g. a nutrient substance.

Figure 3:
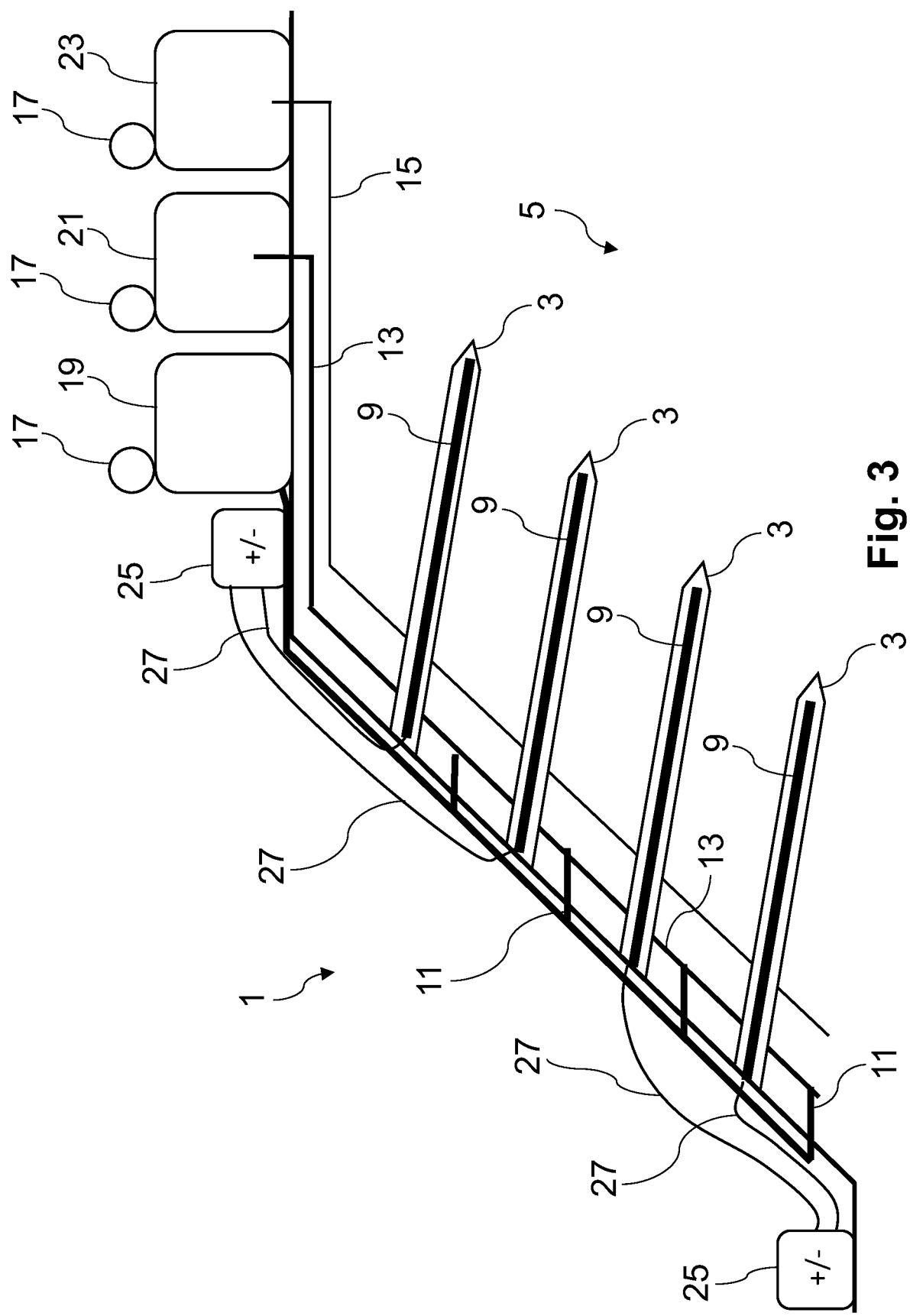
FIG. 3 schematically illustrates in a side view another configuration of the ground consolidation system when applied to an earth slope.

A first variant of the present invention is schematically illustrated in FIG. 3. The configuration of this variant is similar to the configuration of FIG. 1. However, in this variant, the electrodes 9 are placed in a slope. This means that the electrodes are arranged in inclined or semi-inclined positions with respect to at least a portion of the ground surface. Furthermore, only four boreholes are shown in FIG. 3. However, various other ways of arranging the electrodes are possible. This means that the number of electrodes, their depths, lengths, positions in the chambers and/or their distances may be varied depending on the target substance and/or actual application. In this variant, the pipes of the flow network are also arranged somewhat differently compared to the pipe arrangement in FIG. 1. Various ways to arrange the pipes are possible to ultimately provide water (or the consolidation fluids or liquids) to the ground close to anode or positive pole regions and cathode or negative pole regions.

A second variant of the present invention is schematically illustrated in FIG. 4. The configuration of this variant is similar to the configuration of FIGS. 1 and 3. However, in this variant the electrodes 9 are shorter than in the configurations of FIGS. 1 and 3. This means that the electrodes are arranged to move along the longitudinal axis of a respective chamber. Also, the configuration of FIG. 4 shows only one electrode set pair. It is to be noted that in FIG. 4, the chambers 7 are also visible. Furthermore, in this configuration, each one of the three flow systems comprises multiple pipe portions that are substantially parallel with the longitudinal chamber axes. In this manner, it can be guaranteed that the consolidation fluid will be distributed in a large enough ground volume between the electrodes.

The manufacturing process of the proposed electrode system requires minor adjustments compared to existing tools to achieve an external protective coating on the electrodes that resists degradation caused by biological species or the products of their metabolic activity. Therefore, the proposed system is easily reproducible for industrial applications to implement the polarized, bio-geological system of the present invention.

The proposed system of electrodes serves multiple purposes, since except for inducing electric polarization of the ground outside the electrode boreholes to propagate biological species, it can contribute to one or more of the following: (i) grow biofilms through flushing nutrient species to stimulate enzymatic activity; (ii) assist the spatial diffusion of chemical solutes which result in precipitation of cementitious-like minerals when crossing paths with enzymes or other catalysers; (iii) collect and subsequently remove charged ionic byproducts. All the above are implemented in a single set-up without requiring any additional amendments to the positions or the geometry of the electrode systems. The only required modifications relate to the external supply system, which supplies the consolidation fluids to the targeted ground volume, or to the power generators which control the intensity and polarity of the electric field, which is induced by the electrodes.

While the invention has been illustrated, and described in the drawings such description or illustration are to be considered exemplary and not restrictive. Other embodiments and variants are understood and can be achieved by those skilled in the art when carrying out the claimed invention, based on a study of the drawings, the disclosure and the appended claims. In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used.

The invention claimed is:

1. A method for inducing ground consolidation comprising:
providing a first chamber in a first hole in the ground, and a second chamber in a second hole in the ground, the first and second chambers being liquid-impermeable and electrically conductive;
providing a first electrolytic fluid in the first chamber and a second electrolytic fluid in the second chamber;

placing at least a first electrode in the first chamber, and at least a second electrode in the second chamber, the first and second electrodes being operatively connected to a power supply;

feeding one or more consolidation fluids into the ground for feeding one or more reactants of a consolidation process, and one or more catalysers for the one or more reactants into the ground; and applying to the first and second electrodes an electric current causing at least the first electrode to operate as a positive pole and at least the second electrode to operate as a negative pole thereby inducing electric polarisation in the ground to cause the reactants and catalysers to cross paths to thereby cause consolidation of the ground.

2. The method according to claim 1, wherein the one or more consolidation fluids comprise a catalyser fluid comprising an enzymatic catalyser and/or a microorganism, wherein the enzymatic catalyser comprises urease, and/or wherein the microorganism comprises a urease-producing microorganism.

3. The method according to claim 1, wherein the one or more consolidation fluids further comprise a first solute fluid, wherein the first solute fluid is a source of cations acting as a first type of reactants.

4. The method according to claim 3, wherein the first solute fluid comprises calcium compound particles.

5. The method according to claim 3, wherein the first electrode defines a positive pole region in the ground in the vicinity of the first electrode, and wherein the method further comprises feeding the first solute fluid into the positive pole region.

6. The method according to claim 1, wherein the one or more consolidation fluids further comprise a second solute fluid, wherein the second solute fluid is a source of anions acting as a second type of reactants.

7. The method according to claim 6, wherein the second solute fluid comprises urea.

8. The method according to claim 6, wherein the second electrode defines a negative pole region in the ground in the vicinity of the second electrode, and wherein the method further comprises feeding the second solute fluid into the negative pole region.

9. The method according to claim 1, wherein the electric current is a direct current.

10. The method according to claim 1, wherein the method further comprises moving the at least first electrode and/or the at least second electrode along a longitudinal axis of a respective chamber to improve distribution of the one or more reactants and/or catalysers in the ground.

11. The method according to claim 1, wherein the method further comprises reversing polarity of the power source to cause the first electrode to operate as a negative pole and the second electrode to operate as a positive pole.

12. The method according to claim 1, wherein the one or more consolidation fluids are fed into the ground through a pipe network.

13. The method according to claim 1, wherein the method further comprises removing consolidation byproducts from the ground.

14. The method according to claim 13, wherein the removal of the byproducts comprises feeding a third solute fluid comprising base cations acting as byproduct reactants into the ground, wherein the third solute fluid comprises a pH buffer configured to neutralise ammonia.

15. The method according to claim 13, wherein the byproducts are removed by sucking them out of the ground by using a pipe network.

16. The method according to claim 1, wherein the method further comprises feeding a stimulation fluid into the ground for stimulating the activity of the catalysers.

17. The method according to claim 1, wherein the first electrolytic fluid is substantially the same as the second electrolytic fluid.

18. A ground consolidation system comprising:
a first chamber configured to be placed in a first hole in the ground;
a second chamber configured to be placed in a second hole in the ground, the first and second chambers being liquid-impermeable and electrically conductive;
a first electrolytic fluid in the first chamber;
a second electrolytic fluid in the second chamber;
at least a first electrode in the first chamber;
at least a second electrode in the second chamber;
a pipe system configured to be at least partially placed in the ground for feeding one or more consolidation fluids into the ground for feeding one or more reactants of a consolidation process, and one or more catalysers for the one or more reactants into the ground; and
a power supply operatively connected to the at least first electrode and to the at least second electrode, the power source being configured to apply to the at least first and second electrodes an electric current causing the first chamber, the at least first electrode and the first electrolytic fluid to collectively operate as a positive pole, and the second chamber, the at least second electrode and the second electrolytic fluid to collectively operate as a negative pole to thereby induce electric polarisation in the ground to cause the reactants and catalysers to cross paths through attracting and repelling at least the reactants to thereby cause consolidation of the ground.

19. The system according to claim 18, wherein the system further comprises a tank system operatively connected with the pipe system for holding the one or more consolidation fluids, wherein the tank system comprises a first tank and a second tank, different from the first tank, wherein the pipe system comprises one or more pipes configured to extend into the ground, wherein the pipes are configured to extend into the ground between the first and second chambers, and wherein the one or more pipes comprise a set of openings on a surface of a respective pipe for feeding the one or more consolidation fluids into the ground.

20. The system according to claim 18, wherein the system further comprises one or more pumps operatively connected to the tank system for pumping the one or more consolidation fluids into the ground and/or for sucking consolidation byproducts out of the ground.

* * * * *